United States Patent
Niwa et al.

(10) Patent No.: US 9,427,314 B2
(45) Date of Patent: Aug. 30, 2016

(54) INTRAOCULAR LENS INSERTION TOOL

(75) Inventors: Kazuharu Niwa, Nagoya (JP);
Yasuhiko Suzuki, Hashima-gun (JP);
Masayoshi Tanaka, Nagoya (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 191 days.

(21) Appl. No.: 14/342,822

(22) PCT Filed: Sep. 13, 2012

(86) PCT No.: PCT/JP2012/005859
§ 371 (c)(1),
(2), (4) Date: Mar. 5, 2014

(87) PCT Pub. No.: WO2013/038687
PCT Pub. Date: Mar. 21, 2013

(65) Prior Publication Data
US 2014/0228856 A1 Aug. 14, 2014

(30) Foreign Application Priority Data
Sep. 15, 2011 (JP) .................................. 2011-201615

(51) Int. Cl.
*A61F 2/16* (2006.01)

(52) U.S. Cl.
CPC .................................... *A61F 2/167* (2013.01)

(58) Field of Classification Search
CPC .... A61F 2/167; A61F 2/1678; A61F 2/1672; A61F 2/1667; A61F 2/1664; A61F 2/1662; A61F 2/1675
See application file for complete search history.

(56) References Cited

U.S. PATENT DOCUMENTS

| | | | |
|---|---|---|---|
| 6,140,438 A | 10/2000 | Ojio et al. | |
| 7,156,854 B2 * | 1/2007 | Brown | A61F 2/1678 606/107 |
| 8,021,423 B2 * | 9/2011 | Tanaka | A61F 2/1678 606/107 |
| 8,080,017 B2 * | 12/2011 | Tanaka | A61F 2/1664 606/107 |
| 8,123,804 B2 * | 2/2012 | Tanaka | A61F 2/1678 606/107 |
| 8,152,817 B2 * | 4/2012 | Tanaka | A61F 2/1664 606/107 |
| 8,273,122 B2 * | 9/2012 | Anderson | A61F 2/1664 623/6.12 |

(Continued)

FOREIGN PATENT DOCUMENTS

| | | |
|---|---|---|
| EP | 2 074 963 A1 | 7/2009 |
| EP | 2 298 242 A1 | 3/2011 |

(Continued)

OTHER PUBLICATIONS

Jul. 6, 2015 Extended Search Report issued in European Patent Application No. 12832045.4.

(Continued)

*Primary Examiner* — Jonathan Miles
(74) *Attorney, Agent, or Firm* — Oliff PLC

(57) ABSTRACT

An intraocular lens insertion tool including: a cylindrical tool body provided with a placement part at which is placed an intraocular lens having an optical part, and a pair of support parts extending from either side of the optical part; and a plunger for pushing out the intraocular lens; the intraocular lens insertion tool being provided in a state in which the intraocular lens is preset in the placement part, wherein at least one of the front support part extending toward a tip end of the tool body and the rear support part extending toward a rear end of the tool body is pre-deformed by abutting against an abutting projection disposed inside the placement part.

8 Claims, 10 Drawing Sheets

(56) References Cited

U.S. PATENT DOCUMENTS

| | | | |
|---|---|---|---|
| 9,072,601 B2* | 7/2015 | Tanaka | A61F 2/167 |
| 2001/0007942 A1* | 7/2001 | Kikuchi | A61F 2/1672 |
| | | | 606/107 |
| 2003/0209452 A1* | 11/2003 | Mitomo | A45C 11/005 |
| | | | 206/5.1 |
| 2004/0243141 A1* | 12/2004 | Brown | A61F 2/1678 |
| | | | 606/107 |
| 2005/0125000 A1* | 6/2005 | Tourrette | A61F 2/1678 |
| | | | 606/107 |
| 2008/0033449 A1* | 2/2008 | Cole | A61F 2/1691 |
| | | | 606/107 |
| 2009/0171365 A1* | 7/2009 | Tanaka | A61F 2/1664 |
| | | | 606/107 |
| 2009/0171366 A1* | 7/2009 | Tanaka | A61F 2/1664 |
| | | | 606/107 |
| 2009/0292294 A1* | 11/2009 | Tanaka | A61F 2/1678 |
| | | | 606/107 |
| 2009/0318933 A1* | 12/2009 | Anderson | A61F 2/1664 |
| | | | 606/107 |
| 2010/0130985 A1* | 5/2010 | Tanaka | A61F 2/1678 |
| | | | 606/107 |
| 2011/0082463 A1 | 4/2011 | Inoue | |
| 2011/0224677 A1 | 9/2011 | Niwa et al. | |
| 2012/0253356 A1 | 10/2012 | Niwa et al. | |

FOREIGN PATENT DOCUMENTS

| | | |
|---|---|---|
| EP | 2 491 902 A1 | 8/2012 |
| JP | B2-3641110 | 4/2005 |
| JP | A-2006-181269 | 7/2006 |
| JP | A-2009-160138 | 7/2009 |
| JP | A-2009-291399 | 12/2009 |
| WO | 2006/070561 A1 | 7/2006 |
| WO | WO 2008/029498 A9 | 3/2008 |
| WO | 2010/064275 A1 | 6/2010 |
| WO | WO 2011/048631 A1 | 4/2011 |
| WO | 2011/061791 A1 | 5/2011 |

OTHER PUBLICATIONS

International Search Report issued in International Patent Application No. PCT/JP2012/005859 dated Nov. 27, 2012.

Jul. 4, 2016 Office Action issued in Japanese Patent Application No. 2013-533515.

\* cited by examiner

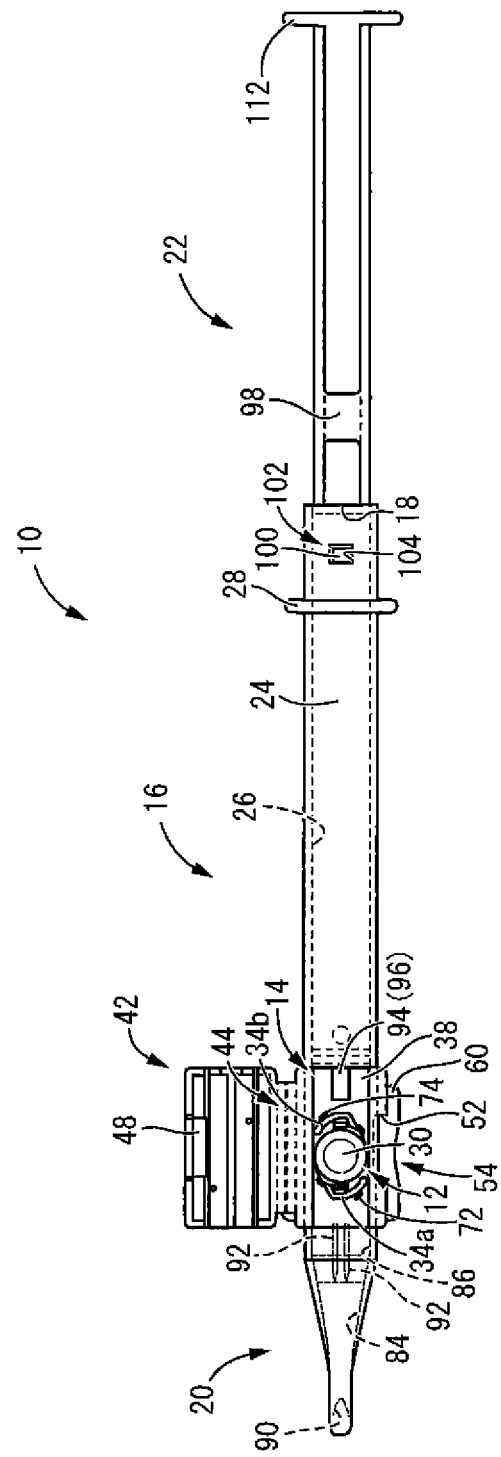

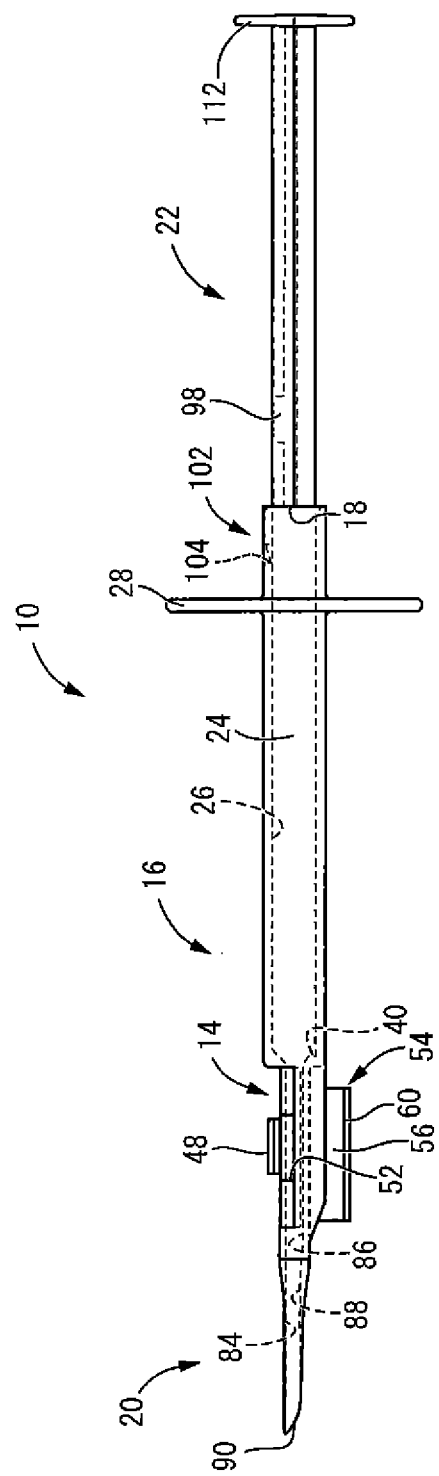

INTRAOCULAR LENS INSERTION TOOL

TECHNICAL FIELD

This invention relates to an intraocular lens insertion tool provided with a preset intraocular lens to be used for inserting the preset intraocular lens into the eye.

BACKGROUND ART

Conventionally, in cataract and other surgery, a method has been adopted wherein a crystalline lens is extracted and removed through an incision made on ocular tissues such as the cornea (sclera) and anterior lens capsule, and thereafter, an intraocular lens is inserted into the eye via the above-mentioned incision to be set in the capsule in lieu of the removed lens.

Especially in recent years, the operation method using an insertion tool for intraocular lenses such as the one described in Patent Document 1 is commonly used. Generally speaking, the intraocular lens is inserted into the eye by means of inserting into the eye the tip opening of an insertion cylinder provided at the tip portion of the tool body through an incision and pushing out the intraocular lens stored in the placement part within the tool body in a compactly deformed condition from the tip opening of the insertion cylinder using an plunger inserted from the base portion of the tool body. Using this type of insertion tool allows an intraocular lens to be inserted without extending the incision formed to extract and remove the crystalline lens, thus saving the time and effort required for the surgical operation and reducing the risk of post-operative astigmatism and infections.

Examples of such an intraocular lens insertion tool include the one provided separately from the intraocular lens in which an individually packed intraocular lens is set up at the time of operation as well as the one provided with a preset intraocular lens. As to the so-called preset type intraocular lens insertion tool provided with a preset intraocular lens, it is to be packaged under sterilized conditions together with the intraocular lens and stored until the time of use.

Therefore, various mechanisms are proposed that can securely support the intraocular lens so as not to deform or damage the intraocular lens stored in the insertion tool for a long time. For example, Japanese Unexamined Patent Publication No. JP-A-2006-181269 (Patent Document 1) proposes to have a protection wall surrounding the intraocular lens project out from the placement part when the tool is not in use so as to prevent the intraocular lens from being subject to stress caused by malfunction of the plunger or the like, and get the protection wall detached when the tool is in use so that the intraocular lens is pushed out by the plunger.

However, even if such a mechanism for securely supporting the intraocular lens under storage is provided, it was sometimes hard to fully stabilize the behavior of the intraocular lens during insertion into the patient's capsule. In other words, the intraocular lens is composed of an optical part and a pair of support parts extending out from either side of the optical part, and these support parts are preset in the placement part so as to extend toward tip and rear ends of the tool body. Therefore, when pushing out the intraocular lens to the insertion cylinder by the plunger, there was a risk that the intraocular lens inserted into the capsule behaves differently, and in some cases, the support parts get damaged and so forth depending on how the front and rear support parts are warped or bent. Especially, in case of the so-called one-piece type intraocular lens wherein the optical part and support parts thereof are integrally formed with a soft synthetic resin material, the hardness of the support parts is subject to change with the temperature or the like, which makes it even harder to stabilize the position of the support parts.

Japanese Unexamined Patent Publication No. JP-A-2009-291399 (Patent Document 2) proposes a structure wherein the front support part abuts against a projection to be bent in a U-shape toward the optical part when the intraocular lens is pushed out by the plunger. This makes it harder for the front support part to move freely when being released from the insertion cylinder, which allows the intraocular lens to be inserted securely into the capsule. However, some intraocular lenses that are pushed out by the plunger in a deformed condition could not be bent in a desired shape without having the front support part engaged with a projection, depending on the hardness of the support part or the displaced preset conditions due to the transport. Also, even if such engagement is successful, there is a risk of not being able to obtain the desired U-shape depending on the hardness of the support part, and there still was a room for improvement in stably controlling the behavior of the support part of the intraocular lens.

BACKGROUND ART DOCUMENTS

Patent Documents

Patent Document 1: JP-A-2006-181269
Patent Document 2: JP-A-2009-291399

SUMMARY OF THE INVENTION

Problem the Invention Attempts to Solve

The present invention was made against the background described above, and the problem to be solved thereby is to provide an intraocular lens insertion tool with a novel structure making it possible to achieve even more stable control over the deformed state of the support part of the intraocular lens.

Means for Solving the Problem

A first mode of the present invention provides an intraocular lens insertion tool comprising: a cylindrical tool body equipped with a placement part where an intraocular lens that has an optical part and a pair of support parts extending from either side of the optical part is placed; and a plunger to be inserted from a rear end part of the tool body to push out the intraocular lens to an insertion cylinder located at a tip portion of the tool body, the intraocular lens insertion tool being provided in a state where the intraocular lens is preset in the placement part so as to have the pair of support parts of the intraocular lens extend toward tip and rear ends of the tool body, wherein at least one of the pair of support parts, that is, a front support part extending toward the tip end of the tool body and a rear support part extending toward the rear end of the tool body, is pre-deformed by abutting against an abutting projection arranged in the placement part.

In the intraocular lens insertion tool with a structure according to the present mode, at least one of the front and rear support parts is preset in the placement part under pre-deformed conditions by abutting against the abutting projection to be warped or bent. This allows the support part to be deformed to the desired shape when the intraocular lens is pushed out from the tool body using the plunger during the surgical operation, thus enabling to properly control the behavior of the support part to prevent any damage thereto and to stabilize the behavior of the intraocular lens within the capsule.

In other words, as to the intraocular lens insertion tool with the conventional structure, it was conceived to stabilize the behavior of the intraocular lens during the surgical operation by means of applying load on the preset intraocular lens as little as possible to avoid deformation thereof. The present invention is based on an entirely novel idea that has never been thought of, and was completed by a breakthrough idea wherein the front and/or rear support parts of the preset intraocular lens are actively deformed during the transport and storage of the insertion tool, and by giving them deforming habits in advance, the desired deformation in shape is induced to the support part of the intraocular lens which is pushed out from the insertion tool during the surgical operation so as to properly control the behavior of the support parts or the intraocular lens. Deformation of the front and/or rear support parts is meant to include an mode wherein the intraocular lens is bent or warped toward the optical part, and an mode wherein the same is deformed toward one side on both sides of the optical axis of the optical part by having the front and/or rear support parts abut against the abutting projection, and an mode of any combination thereof.

A second mode of the present invention is the intraocular lens insertion tool described in the above first mode, wherein at least one of the front and rear support parts is abutted against the abutting projection to be pre-deformed toward the optical part.

In the intraocular lens insertion tool with a structure according to the present mode, at least one of the front and rear support parts is preset in the placement part in a state pre-deformed toward the optical part by abutting against the abutting projection to be warped or bent. Thus, the intraocular lens insertion tool is provided with the intraocular lens preset in the placement part in a state where at least one of the support parts is pre-deformed toward the optical part. Therefore, the support parts are under deformation in the desired shape when the intraocular lens is pushed out from the tool body by the plunger during the surgical operation, thus enabling to properly control the behavior of the support parts to prevent any damage to the intraocular lens, or to stabilize the behavior of the intraocular lens within the capsule.

For example, by means of having the tip portion of the front support part abutted against the abutting projection to be pre-deformed toward the optical part, a state called "tucking" can be favorably generated whereby the tip portion of the front support part is held between the optical part in a state of being deformed by bending in a convex shape when the intraocular lens is pushed out by the plunger. This prevents failures such that the front support part is inserted first when the intraocular lens is released from the insertion cylinder into the capsule to get the intraocular lens inadvertently rotated around the front support part within the capsule, thus enabling to hold the intraocular lens securely within the capsule.

Also, by means of having the tip portion of the rear support part abutted against the abutting projection to be pre-deformed toward the rear surface side of the optical part in a folding manner, the state of tucking can favorably be generated to hold the tip portion of the rear support part between the optical part in a state of being deformed by bending in a convex shape when, the intraocular lens is pushed out by the plunger. Or otherwise, by means of having the tip portion of the rear support part abutted against the abutting projection to be pre-deformed so as to get closer to the front surface side of the optical part, folding of the rear support part in the optical part can be avoided when the intraocular lens is pushed out by the plunger, thus enabling to push out the intraocular lens in a state of having the rear support part extend out toward the rear side of the optical part.

At least one of the front support part and rear support part has only to be abutted against the abutting projection to be pre-deformed, or both of the front and rear support parts can be pre-deformed each being abutted against the abutting projection. Also, the abutting projection can be arranged at any location in the placement part and can include the one integrally provided with the tool body as well as the one provided in a manner detachable from the tool body. In addition, each support part under deformation should shift to get closer to the optical part so as to receive a certain abutting pressure resulting from the abutment against the abutting projection without causing any plastic deformation to each support part.

A third mode of the present invention is the intraocular lens insertion tool described in the first or second mode, wherein the placement part is provided with a plurality of through-holes that open on a placement surface where the intraocular lens is placed while a holding member provided with the abutting projection and a holding projection is assembled to the placement part in a detachable manner so that the holding projection of the holding member protrudes through the through-hole of the placement surface to support the intraocular lens from below, while the abutting projection of the holding member protrudes from the placement surface through the through-hole, and at least one of the front and rear support parts abutted against the abutting projection is pre-deformed toward the optical part.

According to the present mode, an abutting projection is provided to the holding member that is to be assembled to the placement part in a detachable way, and the abutting projection is arranged in the placement part via the through-hole that opens on the placement surface. This allows the intraocular lens to be held securely by assembling the holding projection thereto when the insertion tools are transported and stored in a state of having the intraocular lens preset in, while by means of having the abutting projection abutted against any portion of the front support part and/or rear support part, these support parts can be pre-deformed toward the optical part. Also, when the plunger is pushed out during the surgical operation, by detaching the holding member, the abutting projection can be removed from the placement part together with the holding projection, which makes it possible to avoid interference or the like between the plunger and the abutting projection or the like. Therefore, the abutting projection can be installed at any location with no worries about any interference with the plunger. For example, it is possible to have the abutting projection protrude in the path of the plunger in the push-out direction to make it function as a lock mechanism of the plunger not in use.

A fourth mode of the present invention is the intraocular lens insertion tool described in any of the above first to third modes, wherein the intraocular lens is a one-piece type composed of a soft synthetic resin material.

According to the present mode, since the intraocular lens is integrally formed with a soft synthetic resin material, the pair of support parts have flexibility. Therefore, when each support part is pre-deformed in any direction by the abutting projection during the transport or storage, the post-deformation shape can well be retained after removing the abutting projection, thus achieving the desired deformation of the support part during the push-out by the plunger.

A fifth mode of the present invention is the intraocular lens insertion tool described in any of the above first to fourth modes, wherein the abutting projection is arranged on the placement surface of the placement part where the intraocular lens is placed at a location close to the optical part at one end of the placement surface in a width direction on a front side of the tool body closer to the tip end thereof, and a tip portion of the front support part is abutted against a surface of the abutting projection facing the optical part.

According to the present mode, the tip portion of the front support part is abutted against the front abutting projection to make it closer to the optical part so that the front support part can be deformed toward the optical part side while reducing the load on the front support part. In addition, since the front abutting projection is provided at one end of the placement part in the width direction, the front abutting projection can be arranged avoiding any interference with the plunger even when it is integrally formed with the placement part.

A sixth mode of the present invention is the intraocular lens insertion tool described in any of the above first to fifth modes, wherein the abutting projection is arranged on the placement surface of the placement part where the intraocular lens is placed to protrude from the placement surface at a location close to the optical part at another end of the placement surface in the width direction on a rear side of the tool body closer to the rear end thereof, and a tip portion of the rear support part is abutted against the abutting projection to be deformed toward a front surface side of the intraocular lens.

According to the present mode, the tip portion of the rear support part is abutted against the rear abutting projection to make it closer to the optical part so that the rear support part can be deformed toward the optical part while reducing the load on the rear support part. In addition, since the rear abutting projection protrudes from the placement surface, it is easy to control the tip portion of the rear support part so as to be deformed toward the front surface side of the intraocular lens (upper surface side on the placement surface). Further, since the rear abutting projection is provided on the other end of the placement part in the width direction, the rear abutting projection can be arranged to avoid any interference with the plunger even when integrally formed with the placement part.

A seventh mode of the present invention is the intraocular lens insertion tool described in any of the above first to fifth modes, wherein a lid member is provided in the tool body to cover an opening of the placement part, while in a rear side on a bottom surface of the lid member closer to the rear end of the tool body, the abutting projection is provided protruding from the bottom surface toward the rear support part, and the tip portion of the rear support part is deformed toward a rear surface side of the intraocular lens by the abutting projection.

According to the present mode, the tip portion of the rear support part abuts against the abutting projection to make it closer to the rear surface side of the optical part so that the rear support part can be deformed toward the rear surface side of the optical part while reducing the load on the rear support part. In addition, since the rear abutting projection is provided on the rear surface side of the lid member to protrude therefrom, the rear support part can surely be deformed toward the rear surface side of the optical part in a state of covering the placement part by the lid member.

Effect of the Invention

According to the intraocular lens insertion tool of the present invention, the insertion tool is provided with a preset intraocular lens under a condition where at least one of the front support part and rear support part of the intraocular lens is pre-deformed by abutting against the abutting projection. Thus, the support parts of the intraocular lens pushed out by the plunger during the surgical operation can be deformed in the desired shape, thus enabling to effectively control the behavior of the support parts as well as the intraocular lens.

BRIEF DESCRIPTION OF THE DRAWINGS

FIG. 1 is a top view of an intraocular lens insertion tool as a first embodiment of the present invention.

FIG. 2 is a side view of the insertion tool shown in FIG. 1.

EMBODIMENTS FOR CARRYING OUT THE INVENTION

Figure 3A:
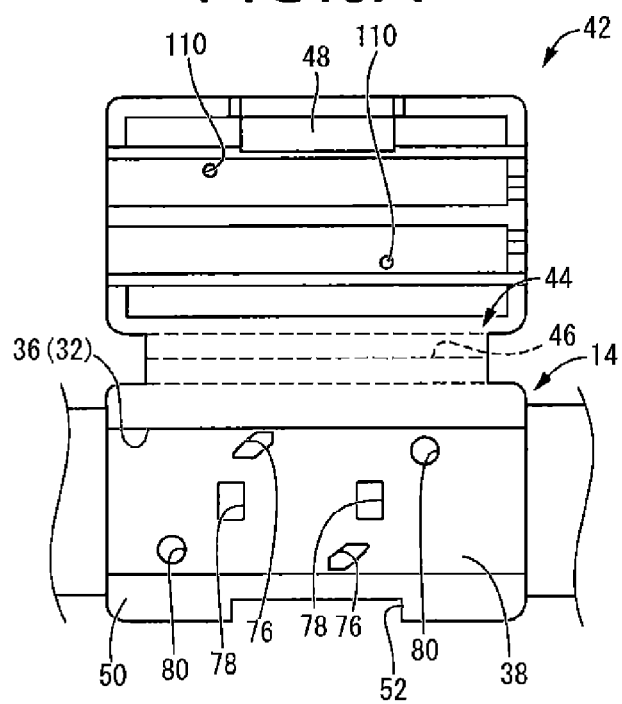
FIGS. 3A and 3B are enlarged top views of key portions of a placement part composing the insertion tool shown in FIG. 1.

In order to further specify the present invention, embodiments thereof will be described below in reference to the drawings.

First of all, FIGS. 1 and 2 show an intraocular lens insertion tool 10 as a first embodiment of the present invention. The intraocular lens insertion tool 10 is made of synthetic resin, comprising a cylindrical tool body 16 provided with a placement part 14 where an intraocular lens 12 is placed and an plunger 22 to be inserted from a rear end part 18 of the tool body 16 for pushing out the intraocular lens 12 to an insertion cylinder 20 placed at the tip portion of the tool body 16, which is offered with the intraocular lens 12 preset therein. In the following descriptions, the phrase "in front of", or "forward" mean "in the push-out direction of the plunger 22" (to the left in FIG. 1), and "upward" means the upper direction in FIG. 2. Also, "left-right direction" means that of the top view of the intraocular lens insertion tool 10 (up is right and down is left in FIG. 1).

In more detail, the tool body 16 has a cylinder body 24 in an approximate shape of a cylinder. Within the cylinder body 24, a through-hole 26 is formed penetrating therethrough in the axial direction with an approximately rectangular cross-section. Also, somewhat in front of the rear end of the cylinder body 24, a plate part 28 is integrally formed to extend in the direction perpendicular to the extension direction of the cylinder body 24.

Figure 3B:
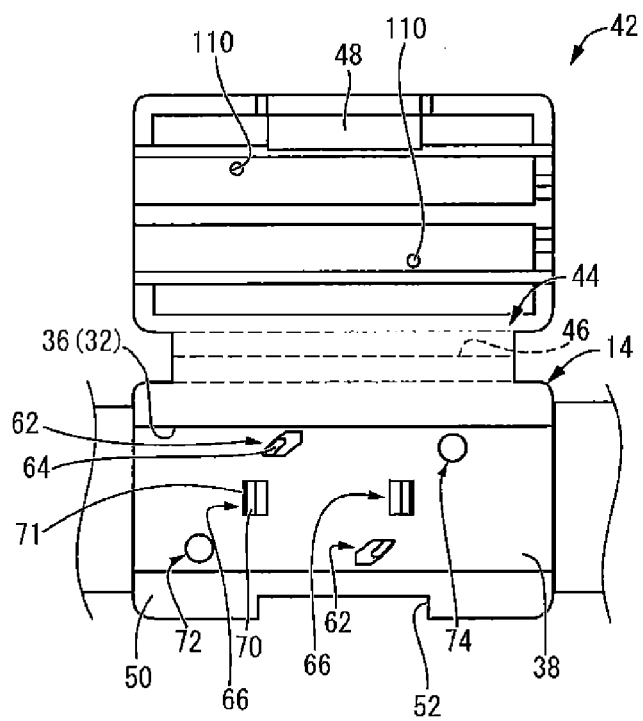

In addition, in front of the cylinder body 24 in the tool body 16, the placement part 14 is formed. FIGS. 3A and 3B show the placement part 14. On the placement part 14, a concave groove 32 is formed to extend in the axial direction with a width slightly larger than the diameter of an optical part 30 of the intraocular lens 12 shown in FIG. 1. The concave groove 32 is formed with a length in the axial direction slightly larger than the maximum width (dimension in the left-right direction in FIG. 1) including a pair of support parts 34a, 34b integrally extending from either side of the optical part 30 of the intraocular lens 12. As to the distinction between the pair of support parts 34a and 34b in the following descriptions, the one that extends out toward the tip end of the tool body 16 is called the front support part 34a, and the other that extends out toward the rear end of the tool body 16 is called the rear support part 34b.

Here, the concave groove 32 has an opening 36 that opens upward, while a placement surface 38 is formed on the bottom surface thereof. The placement surface 38 is made to be a flat plane having a width slightly larger than the minimum width (up-down dimension in FIG. 1) of the intraocular lens 12 and a length in the axial direction larger than the maximum width (dimension in the left-right direction in FIG. 1) of the intraocular lens 12. As to the height, the placement surface 38 is positioned upward from the bottom surface of the through-hole 26 in the cylinder body 24, and at the front edge of the through-hole 26 in the cylinder body 24, a wall part 40 (see FIG. 2) is formed extending upward from the bottom surface of the through-hole 26 to connect to the rear edge of the placement surface 38. Thus, the concave groove 32 is communicated with the through-hole 26, and the width of the concave groove 32 is made approximately the same as that of the through-hole 26.

Then, on the side of the concave groove 32 (right side in the present embodiment), a cover member 42 is integrally formed with the tool body 16 as a lid member. The cover member 42 has a length in the axial direction approximately equal to that of the concave groove 32 and is formed with a width slightly larger than that of the concave groove 32. In addition, the cover member 42 is connected to the tool body 16 by a connecting part 44 in an approximate shape of a thin plate formed by extending the top edge of the placement part 14 toward the side (right side in the present embodiment). The connecting part 44, with its thinnest part at a bending part 46 that extends in the axial direction of the tool body 16 on the center in the width direction, is bendable along the bending part 46. This allows the cover member 42 to cover the opening 36 by having the connecting part 44 bent to overlap on the concave groove 32.

Then, on the edge of the other side of the cover member 42 from the connecting part 44, an engagement piece 48 is formed to protrude, while an edge projection 50 that protrudes outward is formed on the edge of the placement part 14 opposite the cover member 42, and an engagement notch 52 is formed on the edge projection 50 at a position corresponding to the engagement piece 48.

Figure 4:
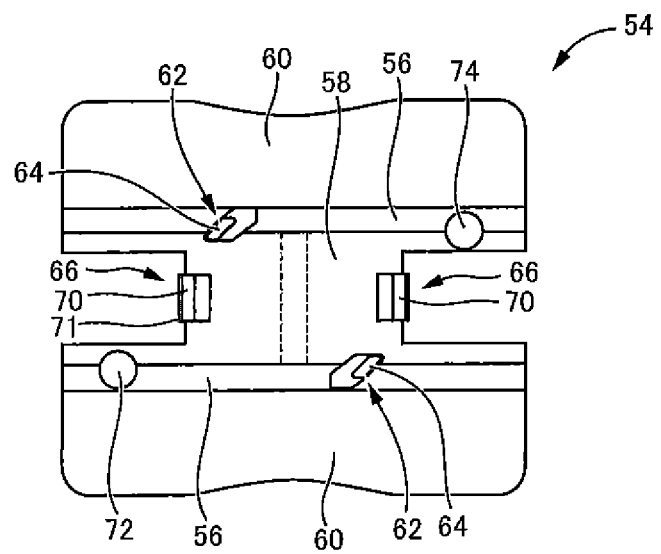
FIG. 4 is a top view of a holding member composing the insertion tool shown in FIG. 1.
Figure 5:
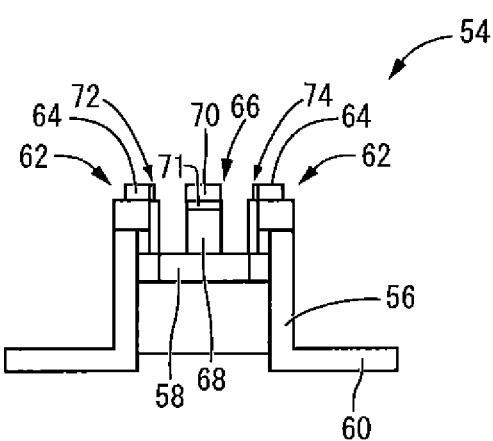
FIG. 5 is a side view of the holding member shown in FIG. 4.

Under the placement surface 38 of the placement part 14 with the structure described above, a holding member 54 is provided in a detachable manner in a state of supporting the intraocular lens 12. As shown in FIGS. 4 and 5, the holding member 54 is configured as a component separate from the tool body 16 to form a structure wherein a pair of side walls 56, 56 are connected by a connecting plate 58 integrally formed between their opposing surfaces. Here, the distance between the outer surfaces of the side walls 56 is made approximately the same as the diameter of the optical part 30 of the intraocular lens 12. Also, at the bottom of each side wall 56, a leg plate 60 is integrally formed being bent to the outside. Each leg plate 60 is formed with a slight hollow in the top view around the center in the axial direction.

Then, on top of each of the side walls 56, 56, a pair of first holding projections 62, 62 are integrally formed to protrude upward in an approximate shape of an arc in the top view. In addition, a peripheral wall 64 is integrally formed to protrude from the inside of the holding member 54 on the outside of the top surface of each first holding projection 62. Here, the distance between the peripheral walls 64 is made slightly larger than the diameter of the optical part 30 of the intraocular lens 12.

Also, at both ends of the connecting plate 58 in the axial direction, a pair of second holding projections 66, 66 are integrally formed to protrude upward in a shape of a rectangular in the top view at opposite positions separated from each other in the longitudinal direction (left-right direction in FIG. 4). Here, the height of the top surface of the second holding projection 66 is made the same as that of the top surface of the first holding projection 62. Each second holding projection 66 comprises a projection body 68 that protrudes from the connecting plate 58, a peripheral wall 70 that protrudes from the top surface of the projection body 68, and an engagement part 71 provided to protrude outward in the facing direction of the second holding projection 66 on the upper side surface of the projection body 68. The distance between the peripheral walls 70, 70 in the facing direction is made slightly larger than the diameter of the optical part 30 of the intraocular lens 12. In addition, each peripheral wall 70 and each engagement part 71 have approximately the same width dimensions as that of the projection body 68.

Further, in the holding member 54, a front abutting projection 72 in an approximate shape of a cylinder, against which the front support part 34a is to be abutted, is integrally formed to protrude at a location close to the side wall 56 at one end in the width direction (downside in FIG. 4) on the front side of the tool body 16 closer to the tip end thereof than the second holding projection 66. Also in the holding member 54, a rear abutting projection 74 in an approximate shape of a cylinder, against which the rear support part 34b is to be abutted, is integrally formed to protrude at a location close to the side wall 56 at the other end in the width direction (upside in FIG. 4) on the rear side of the tool body 16 closer to the rear end thereof than the second holding projection 66.

The holding member 54 with the structure described above is made to be assembled from under the placement surface 38 of the tool body 16. More specifically, on the placement surface 38 of the tool body 16, through-holes 76, 78, 80 are formed opening to the placement surface 38 where the intraocular lens 12 is placed (see FIG. 3A). Then, by having the first and second holding projections 62, 66 of the holding member 54 protrude through the through-holes 76, 78, the holding member 54 supports from below the outer periphery of the optical part 30 of the intraocular lens 12. Also, the front abutting projection 72 and the rear abutting projection 74 are arranged to protrude from the placement surface 38 penetrating through the through-holes 80.

In more detail, the through-holes 76, 78 are in approximately the same shape as the cross-sections of the first and second holding projections 62, 66, being formed to penetrate through the placement surface 38 in a slightly larger outer dimension than said holding projections 62, 66. Also, the through-hole 80 has a circular cross-section corresponding to the front and rear abutting projections 72, 74, being formed to penetrate through the placement surface 38 in a slightly larger dimension than said abutting projections 72, 74. Then, the first and second holding projections 62, 66 are inserted through the through-holes 76, 78 from under the placement surface 38 to protrude therefrom. This allows the holding member 54 to be assembled to the tool body 16 from its outside by having the engagement part 71 provided on the second holding projection 66 protrude from the placement surface 38 to be engaged with the top surface thereof so that the first holding projection 62 and the second holding projection 66 are held in a state of protruding from the placement surface 38. In addition, the front and rear abutting projections 72, 74, together with the first and second holding projections 62, 66, are inserted through the through-hole 80 from under the placement surface 38 to protrude therefrom. The engagement of the above-mentioned engagement part 71 is configured such that the holding member 54 can be pulled out by extracting the holding member 54 downward from the placement surface 38.

Further, in front of the placement part 14, an insertion cylinder 20 is integrally formed to extend forward in the axial direction of the tool body 16. The insertion cylinder 20 is in a tapered shape as a whole gradually decreasing in diameter from the side of the placement part 14 toward the tip portion in the extending direction, in which a through-hole 84 in a tapered shape is formed penetrating through the entire length in the same direction.

The through-hole 84 communicates with the placement part 14 by having a base opening 86 that opens to the side of the placement part 14 connected to the placement surface 38. The base opening 86 has a bottom surface 88 in a flat plane and a top surface in an approximate shape of an arc so as to have a flat, approximately oval cross-section as a whole. The tip portion of the through-hole 84 is provided with a tip end opening 90 that is made to be a beveled opening with the top surface extending further forward than the bottom surface.

Also, on the bottom surface 88, guiding projections 92 are formed extending in the axial direction of the tool body 16 with the widthwise center of the bottom surface 88 in between. The guiding projections 92 are made in a linear shape extending in parallel to each other slightly protruding upward from the bottom surface 88. The protrusion height of the guiding projection 92 gradually increases as it goes forward in the axial direction of the tool body 16 and becomes flush with the bottom surface 88 at the rear end of the base opening 86.

Moreover, the guiding projections 92 are arranged approximately in parallel with the widthwise center of the bottom surface 88 in between, being separated from each other at a given distance in the transaxial direction of the tool body 16, and such distance between the guiding projections 92 is preferably slightly larger than the width dimension of the tip portion of the plunger 22, and especially in the present aspect, is made slightly larger than the width dimension of a rod-like part 94 of the plunger 22.

As described above, the tool body 16 of the present embodiment is configured as a single member integrally formed with the cylinder body 24, placement part 14, cover member 42, and insertion cylinder 20, wherein the holding member 54 configured as a component separate from the tool body 16 can be assembled from under the placement surface 38.

Then, from the rear end of the tool body 16, the plunger 22 is inserted into the through-hole 26. The plunger 22 is made in an approximate shape of a rod having a slightly larger length than that of the tool body 16 in the axial direction, and a working part 96 in an approximate shape of a cylinder and an insertion part 98 in an approximate shape of a rectangular rod are integrally formed.

In the intraocular lens insertion tool 10 with the structure described above, the tip portion of the plunger 22 is inserted into the cylinder body 24 of the tool body 16 from the rear end to be set at the initial position where a pawl part 100 is locked in a locking hole 104 of a locking part 102. At the same time, the holding member 54 is attached to the tool body 16 from under the placement surface 38 to be temporarily held therein, as described above. This allows the holding member 54 to be assembled to the tool body 16 to temporarily hold the first holding projection 62, second holding projection 66, front abutting projection 72, and rear abutting projection 74 of the holding member 54 protruding from the placement surface 38.

Figure 6:
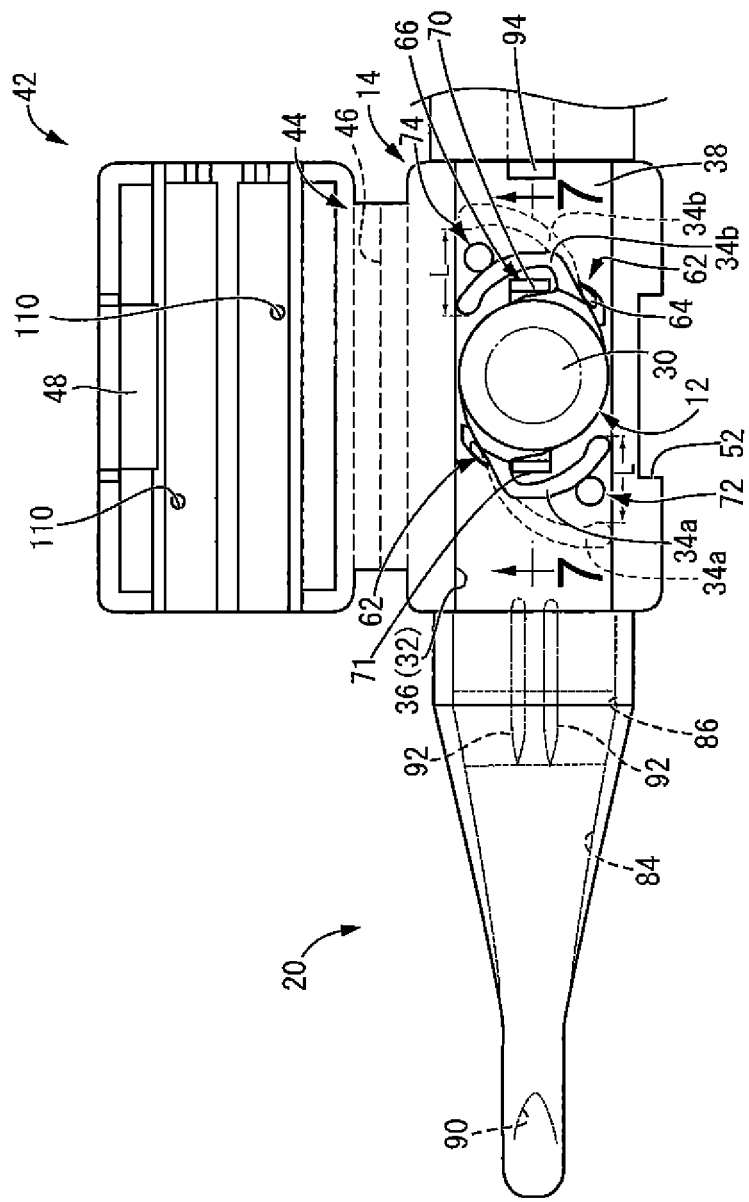
FIG. 6 is an enlarged top view illustrating key portions of the insertion tool shown in FIG. 1.

As shown in FIG. 6, the optical part 30 of the intraocular lens 12 is placed on the top surface of the first holding projection 62 and second holding projection 66. In FIG. 6, only relevant portions of the tool body 16, the intraocular lens 12, the holding member 54, and the tip portion of the plunger 22 reaching inside the placement part 14 are shown for better understanding. In such a state of placement, the optical part 30 of the intraocular lens 12 is in contact with the first and second holding projections 62, 66 along the outer periphery, and the central portion is held in no contact with the first and second holding projections 62, 66. Also, with the plunger 22 at its initial position, in front of the rod-like part 94 at the tip portion of the plunger 22 in the axial direction (to the left in FIG. 6), the second holding projection 66 is arranged facing back toward it. In other words, in the present embodiment, a stopper that prevents the plunger 22 from going forward is composed of the second holding projection 66 so that the plunger 22 cannot go forward unless the second holding projection 66 recedes from the placement surface 38.

Further, the peripheral walls 64, 70 formed on the first and second holding projections 62 and 66 are located outside the optical part 30 of the intraocular lens 12, and especially in the present embodiment, the peripheral wall 64 formed on the first holding projection 62 holds the intraocular lens 12 from both sides in the direction tilted from the axial direction of the tool body 16, while the peripheral wall 70 formed on the second holding projection 66 holds the intraocular lens 12 from both sides in the axial direction of the tool body 16. This restricts the amount of displacement of the intraocular lens 12 relative to the tool body 16 both in the axial and transaxial directions, thus enabling to securely hold the intraocular lens 12.

In addition, in a state of placement on the first and second holding projections 62, 66, the optical part 30 of the intraocular lens 12 is placed away from the placement surface 38 at a given distance so as to be held in no contact with the placement surface 38.

Here, the front abutting projection 72 and the rear abutting projection 74 provided close to the second holding projections 66, 66 are also arranged close to the optical part 30 of the intraocular lens 12 that is held by the first and second holding projections 62, 66. As clearly shown in FIG. 6, the front support part 34a and the rear support part 34b are arranged to abut against the surfaces of the front abutting projection 72 and the rear abutting projection 74 both facing the optical part 30. As a result, the front support part 34a and the rear support part 34b are deformed to bend or warp so as to get closer to the optical part 30. Thus, in the intraocular lens insertion tool 10 of the present embodiment, the front support part 34a and the rear support part 34b of the intraocular lens 12 are preset in the placement part 14 being pre-deformed so as to get closer to the optical part 30 by means of abutting against the front abutting projection 72 and the rear abutting projection 74, respectively. Since the front abutting projection 72 and the rear abutting projection 74 are made in an approximate shape of a cylinder with no protrusion on the outer periphery thereof, the front support part 34a and the rear support part 34b are favorably prevented from being damaged by the abutting pressure against the front abutting projection 72 and the rear abutting projection 74.

Also, any method can be used to let the front support part 34a and the rear support part 34b abut against the front abutting projection 72 and the rear abutting projection 74. For example, the front support part 34a and the rear support part 34b as indicated in the dashed line in FIG. 6, which are in an initial shape before deformation with no stress applied, can be moved by means of grabbing the tip portions thereof by rod-like parts (not shown in the drawing) to make them abut against the front abutting projection 72 and the rear abutting projection 74, respectively. The amount of displacement L before and after the deformation of each front tip portion of the support parts 34a, 34b in the axial direction of the tool body 16 (see FIG. 6) is preferably 0.05 to 3 mm, and more preferably 0.5 to 2 mm. In short, the deformation of each of the support parts 34a, 34b is generated from its shift to get closer to the optical part 30 to undergo flexural deformation by being pushed toward the optical part 30 due to abutment reaction force against the abutting projections 72, 74 respectively, which does not cause plastic deformation.

Figure 7:
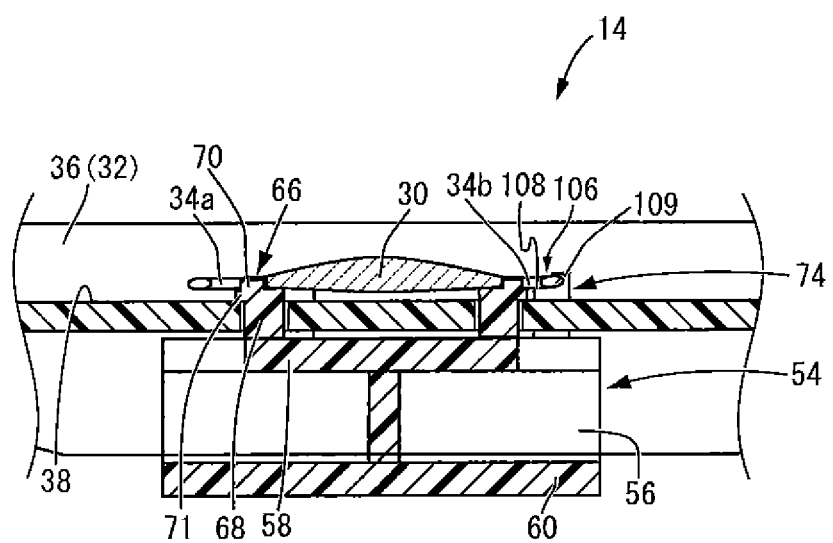
FIG. 7 is an enlarged longitudinal cross-sectional view taken along line 7-7 of FIG. 6 showing the key portions.

Moreover, as shown in FIG. 7, the rear abutting projection 74 is in a stepped shape with a notch part 106 extending upward from the midpoint in the projecting direction, and the middle portion of the rear support part 34b in the length direction is placed on a stepped part 108 to be supported upward in FIG. 7, which is toward the front surface side of the optical part 30, while the tip portion of the rear support part 34b is guided by a peripheral wall 109 of the notch part 106 toward the optical part 30 to be deformed so as to get closer to the front surface side of the optical part 30.

Thus, the intraocular lens 12 is preset in the placement part 14 in a state where the front support part 34a and the rear support part 34b of the intraocular lens 12 are abutted against the front abutting projection 72 and rear abutting projection 74, respectively, to be pre-deformed so as to get closer to the optical part 30. Thereafter, the intraocular lens 12 is set in the tool body 16 in a stored state by having the bending part 46 bent to cover the opening 36 of the placement part 14 with the cover member 42. The cover member 42 remains at a closing position by engaging the engagement piece 48 with the engagement notch 52.

The intraocular lens 12 is stored in the insertion tool 10 in the way described above. The insertion tool 10 of the present embodiment is packaged and distributed after being treated with sterilization with the intraocular lens 12 stored therein.

The insertion tool 10 of the present embodiment provided with the preset intraocular lens 12 in this way is used for cataract and other surgery in the following way:

After unpacking the insertion tool, it is preferable to inject lubricant consisting mainly of viscoelastic materials such as sodium hyaluronate into the interior of the placement part 14 and insertion cylinder 20. Especially in the present embodiment, the cover member 42 is provided with an injection hole 110 penetrating therethrough in the thickness direction so that the lubricant can be injected into the hole with the cover member 42 closed. However, the lubricant can also be injected, for example, from the tip end opening 90 of the insertion cylinder 20 or the opening 36 of the placement part 14 with the cover member 42 opened, or otherwise from the rear end part 18 at the rear end of the through-hole 26 after extracting the plunger 22 from the tool body 16.

Next, by extracting the holding member 54 downward from the tool body 16, the temporary holding by the convex and concave engagement is released so as to remove the holding member 54 from the tool body 16. This allows the intraocular lens 12 to be placed on the placement surface 38 in a state surrounded by the above-mentioned lubricant. Here, the intraocular lens 12 is a one-piece type wherein the optical part 30 and the pair of support parts 34a, 34b are integrally composed of a soft synthetic resin material as shown in Japanese Patent No. 3641110. Therefore, the front support part 34a and the rear support part 34b have flexibility, and even if the support parts 34a, 34b are abutted against the front and rear abutting projections 72, 74, respectively, and held for a certain period during packaging and transport in a state pre-deformed to get closer to the optical part 30, the plastic deformation is not caused, although the deformation is not immediately released when the holding member 54 is removed in a state of being surrounded by viscous lubricant so that the deformation is more or less maintained until the plunger 22 is pushed in. Since the placement surface 38 of the present embodiment is made to be a flat plane, the intraocular lens 12 can be securely placed thereon, while rotation of the intraocular lens 12 on the placement surface 38 in the circumferential direction can be prevented because the width dimension of the concave groove 32 is made slightly larger than the diameter of the optical part 30 of the intraocular lens 12.

Subsequently, a pressing plate 112 of the plunger 22 is pushed into the tool body 16 in a state where the tip portion of the insertion cylinder 20 is inserted into the incision made on the ocular tissues. This allows the rod-like part 94 at the tip portion of the plunger 22 to abut against the outer periphery of the optical part 30 of the intraocular lens 12 placed on the placement surface 38 so that the intraocular lens 12 is guided by the plunger 22 toward the insertion cylinder 20 to be sent out from the tip portion of the insertion cylinder 20 into the capsule. The maximum push-in distance is restricted by the tip end surface of the insertion part 98 being engaged with the wall part 40 of the through-hole 26, and the tip portion of the plunger 22 is made to protrude slightly from the tip end opening 90 at the maximum push-in position.

In the intraocular lens insertion tool 10 with the structure according to the present embodiment, the abutting projections 72, 74 are provided in the holding member 54. Therefore, by means of having the tip portion of the front support part 34a abutted against the front abutting projection 72 to be pre-deformed toward the optical part 30, a state called "tucking" can be favorably generated whereby the tip portion of the front support part 34a is held between the optical part 30 deformed to bend in a convex shape by passing through the guiding projections 92 when the intraocular lens 12 is pushed out by the plunger 22. This prevents failures such that the front support part 34a is inserted first when the intraocular lens 12 is released from the insertion cylinder 20 into the capsule to get the intraocular lens 12 inadvertently rotated around the front support part 34a within the capsule, thus enabling to hold the intraocular lens 12 securely within the capsule.

Also, the tip portion of the rear support part 34b is abutted against the rear abutting projection 74 to be pre-displaced toward the optical part 30. Especially in the present embodiment, the middle portion of the rear support part 34b in the length direction is placed on the stepped part 108 of the rear abutting projection 74, while being deformed so as to get closer to the front surface side of the optical part 30 by the guidance of the peripheral wall 109. Therefore, folding of the rear support part 34b in the optical part 30 can be avoided when the intraocular lens 12 is pushed out by the plunger 22, thus enabling to push out the intraocular lens 12 in a state where the rear support part 34b extends out toward the rear side of the optical part 30. This allows the cross-sectional area of the intraocular lens 12 compactly folded in the insertion cylinder 20 to be smaller, thus enabling to release the intraocular lens 12 smoothly from the insertion cylinder 20.

In the present embodiment, the intraocular lens 12 is positioned and placed on the holding projections 62, 66 of the holding member 54 that are formed separately from the tool body 16 and assembled thereto. Also, the holding member 54 is provided with the front abutting projection 72 and the rear abutting projection 74 where the tip portions of the front support part 34a and the rear support part 34b of the intraocular lens 12 are abutted against. Therefore, the holding member 54 makes it possible to securely hold the intraocular lens 12 during the transport and storage, whereas during the surgical operation, the abutting projections 72, 74 can each be removed from the placement surface 38 by extracting the placement part 14 from the holding member 54. Therefore, the interference between each of the abutting projections 72, 74 and the plunger 22 can be avoided, thus improving the degree of design freedom of the abutting projections 72, 74.

Since the intraocular lens 12 is composed of a soft synthetic resin material, the support parts 34a, 34b are each flexible with a comparatively low elasticity. Therefore, by having the front and rear support parts 34a, 34b abutted against the abutting projections 72, 74 to be pre-deformed during the transport and storage, the deformed shape of the support parts can be fully maintained after the removal of the front and rear abutting projections 72, 74. Therefore, the desired deformation of the front support part 34a and the rear support part 34b can be achieved during pushing out by the plunger 22.

In addition, since the tip portion of the front support part 34a is abutted against the front abutting projection 72 to get closer to the optical part 30, it is possible to deform the front support part 34a toward the optical part 30 while reducing the load thereon.

An embodiment of the present invention has been described in detail above, but it is only exemplary and the present invention should never be interpreted by those specific descriptions of the embodiment in a limited way.

Figure 8A:
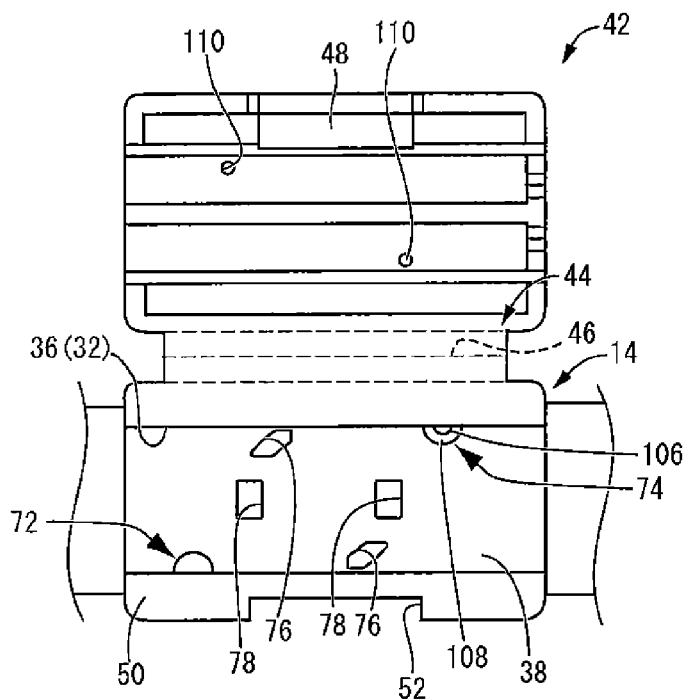
FIGS. 8A and 8B are enlarged top views showing another aspect of the placement part composing the insertion tool of the present invention.
Figure 8B:
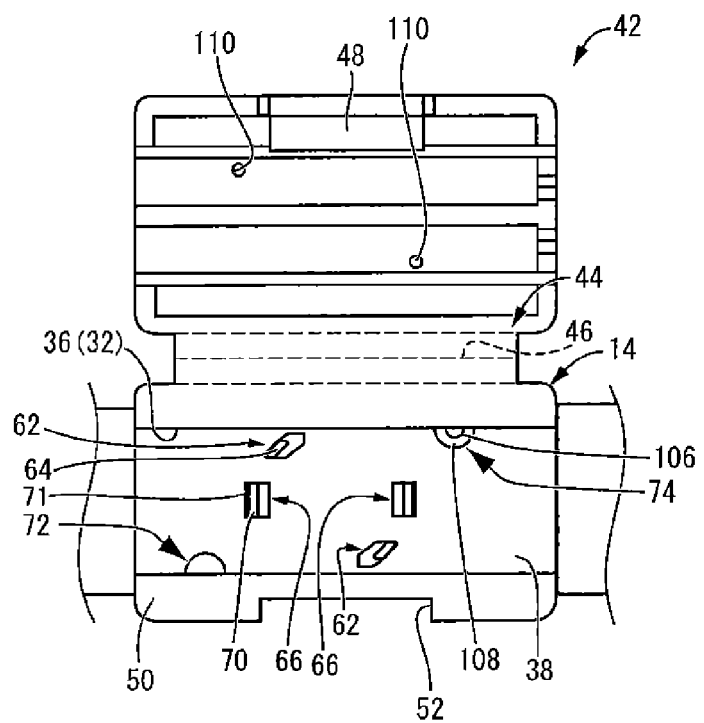

For example, in the first embodiment, the holding member 54 formed separately from the tool body 16 was provided with the front abutting projection 72 and the rear abutting projection 74, but for example, as shown in FIGS. 8A and 8B, the front abutting projection 72 and the rear abutting projection 74 can be configured as convex parts integrally formed with the side walls of the placement part 14 of the tool body 16 protruding therefrom. In such a structure, a state can surely be maintained where the front support part 34a and the rear support part 34b are abutted against the front abutting projection 72 and the rear abutting projection 74 to be deformed toward the optical part 30 even after the holding member 54 is removed. Therefore, the present invention can be favorably applied to a case, for example, where a two-piece type intraocular lens 12 is preset in the insertion tool having the optical part 30 and the pair of support parts 34a, 34b configured by members different from each other and the support parts 34a, 34b have comparatively higher elasticity. The rear abutting projection 74, as in the first embodiment, is in a stepped shape with a notch part 106 extending upward from the midpoint in the projecting direction, and the tip portion of the rear support part 34b is placed on a stepped part 108 to be supported under deformation toward the front surface side of the optical part 30. Also, in the aspect of the first embodiment or FIGS. 8A and 8B, both the front support part 34a and the rear support part 34b are abutted against the abutting projections 72, 74 to be pre-deformed, but only one of the support parts that needs a control over deformation can be pre-deformed.

Figure 9:
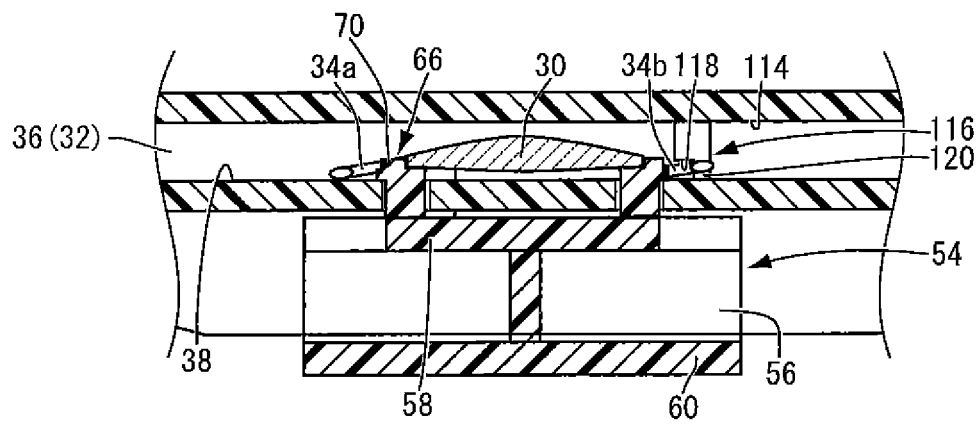
FIG. 9 is an enlarged cross-sectional view of key portions showing another aspect of a rear abutting projection composing the insertion tool of the present invention, which corresponds to FIG. 7.

Although in the aspect of the first embodiment or FIGS. 8A and 8B, the tip portion of the rear support part 34b was deformed so as to get closer to the front surface side of the optical part 30, the tip portion of the rear support part 34b can also be folded to the rear surface side of the optical part 30. More specifically, as shown in FIG. 9, it is possible to have a rear abutting projection 116 protrude toward the rear support part 34b from a bottom surface 114 of the cover member 42 in its rear side (to the right in FIG. 9) forming a stepped shape with a notch from the midpoint downward in the protruding direction so that the middle portion of the rear support part 34b in the length direction is pressed down against a stepped part 118, while the tip portion of the rear support part 34b is deformed by a peripheral wall 120 of the notch as if it gets into the rear surface side of the optical part 30. This allows the "tucking" state to be favorably generated wherein the tip portion of the rear support part 34b is held between the optical part 30 deformed by bending in a convex shape when the intraocular lens 12 is pushed out by the plunger 22. Also, it is made possible to favorably prevent failures such that the tip portion of the rear support part 34b is get caught inside the tool body 16 or some other portion to generate cracks in the rear support part 34b during the push-out by the plunger 22. Abutment of the rear support part 34b against the rear abutting projection 116 can easily be achieved by means of closing the cover member 42 under a condition where the tip portion of the rear support part 34b of the intraocular lens 12 stored in the placement part 14 is bent in advance as if it gets into the rear surface side of the optical part 30. In other words, the rear support part 34b that gradually recovers to the initial state after the closure of the cover member 42 is abutted against the rear abutting projection 116 to maintain such a deformed state.

Further, in the first embodiment or in the variations shown in FIGS. 8A, 8B and 9, the front support part 34a and the rear support part 34b were each abutted against the single abutting projections 72 and 74 or 116, respectively to be deformed toward the optical part 30, but a plurality of abutting projections can be abutted against multiple locations of the support parts 34a, 34b to be deformed by bending or warping in advance.

In addition, in the first embodiment or in the variations shown in FIGS. 8A, 8B and 9, the front support part 34a and the rear support part 34b were preset in the insertion tool 10 under deformation toward the optical part 30 by being abutted against the front abutting projection 72 and the rear abutting projection 74 or 116, respectively, but the front support part 34a and the rear support part 34b do not necessarily have to be deformed toward the optical part 30 and can be deformed toward either direction along the optical axis (upward or downward in FIG. 7). More specifically, although not shown in the drawing, it is possible to have a front abutting projection with a structure similar to that of the rear abutting projection 116 shown in FIG. 9 protrude from the bottom surface 114 of the cover member 42 in its front side toward the front support part 34a to be deformed downward (bottom side in FIG. 7) along the optical axis of the optical part 30 without moving the front support part 34a closer to the optical part 30. By doing this, when the intraocular lens 12 is pushed out from the insertion tool 10 by the plunger 22, the "tucking" state can be achieved by means of controlling the front support part 34a to be folded to the rear surface side of the optical part 30 of the intraocular lens 12. Also, it is possible to arrange the rear abutting projection 74 shown in FIGS. 8A and 8B in the rear away from the optical part and deform the rear support part 34b only upward (top side in FIG. 7) along the optical axis of the optical part 30 without moving the rear support part 34b closer to the optical part 30. By doing this, when the intraocular lens 12 is pushed out from the insertion tool 10 by the plunger 22, the folding of the rear support part 34b in the optical part 30 can be avoided by means of controlling the rear support part 34b to be deformed toward the front surface side of the optical part 30 of the intraocular lens 12. Also, it is possible to arrange the rear abutting projection 116 shown in FIG. 9 in the rear away from the optical part and deform the rear support part 34b downward (bottom side in FIG. 7) along the optical axis of the optical part 30 without moving the rear support part 34b closer to the optical part 30. By doing this, when the intraocular lens 12 is pushed out from the insertion tool 10 by the plunger 22, the rear support part 34b can be protected by means of controlling the rear support part 34b to be deformed as if it is folded to the rear surface side of the optical part 30 of the intraocular lens 12.

Next, key components of an intraocular lens insertion tool 122 as another embodiment of the present invention will be described below in reference to FIGS. 10 and 11. The present embodiment replaces the rear abutting projection 74 integrally provided with the holding member 54 in the intraocular lens insertion tool 10 of the first embodiment with a rear abutting projection 124 projecting from the placement surface 38 so as to make the rear support part 34b of the intraocular lens 12 retainable in high precision. In the following descriptions, details will be omitted for members and parts substantially similar to those of the above-mentioned embodiments by assigning like symbols.

Figure 10:
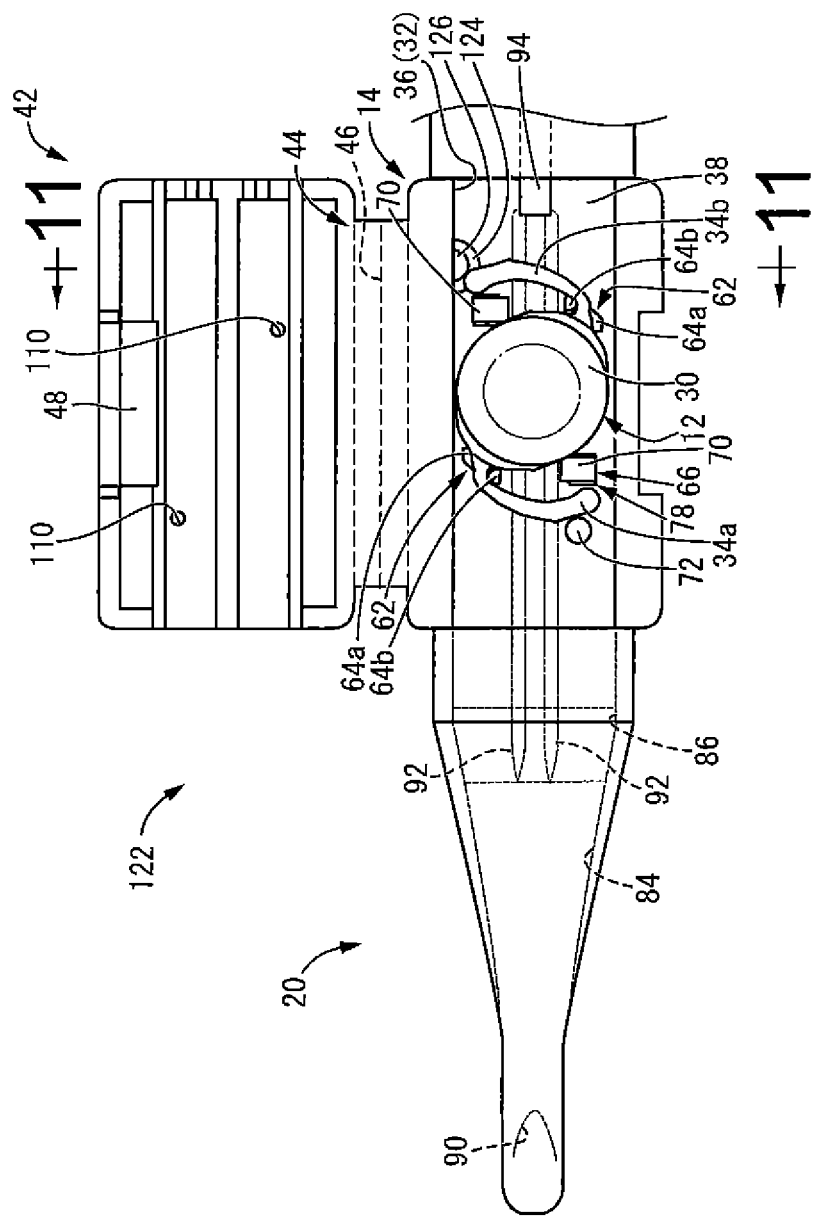
FIG. 10 is an enlarged top view showing another aspect of the insertion tool of the present invention, which corresponds to FIG. 6.
Figure 11:
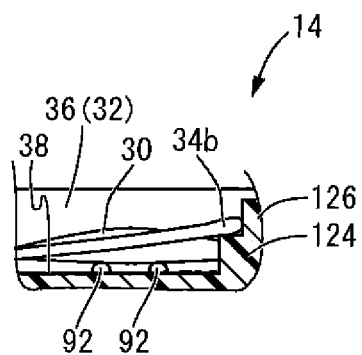
FIG. 11 is an enlarged cross-sectional view taken along line 11-11 of FIG. 10 showing key portions.

In more detail, as shown in FIG. 10, the intraocular lens insertion tool 122 of the present invention is such that the peripheral wall 64 on the first holding projection 62 that protrudes from the placement surface 38 penetrating through the bottom surface of the concave groove 32 of the tool body 16 is divided into two sections so that the front and rear support parts 34a, 34b of the intraocular lens 12 are held between the peripheral walls 64a, 64b at portions near the optical part 30. Also, the front support part 34a is arranged to abut against the front abutting projection 72 on the surface facing the optical part 30. As a result, the front support part 34a is deformed by bending or warping to get closer to the optical part 30. In addition, the rear abutting projection 124 is provided in an approximate shape of a cylinder, on which is a projection 126 in an approximate shape of a cylinder with a smaller radius about the same axis. Then, the rear support part 34b is arranged to abut against the projection 126 of the rear abutting projection 124 on the surface facing the optical part 30. As shown in FIG. 11 as an enlargement of the key portions, the top surface of the rear abutting projection 124 provided with the projection 126 is approximately at the same height as the top surface of the optical part 30. For better understanding, the figure shows only the concave groove 32, optical part 30, rear support part 34b, placement surface 38, guiding projections 92, rear abutting projection 124, and projection 126. In the present embodiment, since the rear abutting projection 124 arranged on the placement surface 38 remains as it is when the intraocular lens 12 is pushed out by the rod-like part 94 of the plunger 22, unlike the case of the rear abutting projection 74 of the first embodiment, the rear support part 34b can be deformed more securely toward the upper side of the optical part 30 to be placed thereon.

Also, in the intraocular lens insertion tool 122 of the present embodiment, the guiding projections 92 extend on the placement surface 38 all the way across the length thereof in the axial direction of the tool body 16 with the widthwise center of the bottom surface 88 in between. This allows the intraocular lens 12 placed on the rod-like part 94 of the plunger 22, which is on the above-mentioned placement surface 38, to be guided in high precision in the axial push-out direction. The bottom surface of the optical part 30 is abutted against the top surface of the guiding projections 92 under a condition where the intraocular lens 12 is held on the first and second holding projections 62, 66.

Although not all examples will be exhausted herein, the present invention can be implemented in various aspects after changes, modifications and improvements and so forth based on the knowledge of those skilled in the art, and needless to say, such aspects of the embodiments should be included in the scope of the present invention as long as they do not deviate from the spirit of the present invention.

KEYS TO SYMBOLS

10: Insertion tool, 12: Intraocular lens, 14: Placement part, 16 Tool body,
18: Rear end part, 20: Insertion cylinder, 22: Plunger,
30: Optical part, 32: Concave groove, 34a: Front support part,
34b: Rear support part, 36: Opening, 38: Placement surface,
42: Cover member, 44: Connecting part, 54: Holding member,
56: Side wall, 62: First holding projection, 66: Second holding projection,
72: Front abutting projection, 74: Rear abutting projection,
76: Through-hole, 78: Through-hole, 80: Through-hole, 106: Notch part,
108: Stepped part, 109: Peripheral wall, 114: Bottom surface,
116: Rear abutting projection 118: Stepped part, 120 Peripheral wall

The invention claimed is:
1. An intraocular lens insertion tool comprising:
a cylindrical tool body that includes a placement part and an abutting projection, the placement part being configured to receive an intraocular lens having an optical part and a pair of support parts extending from either side of the optical part;
an insertion cylinder located at a tip portion of the tool body; and
a plunger that is inserted from a rear end of the tool body to push the intraocular lens from the tool body and to the insertion cylinder;
wherein:
the pair of support parts of the intraocular lens include a first support part and a second support part, the intraocular lens insertion tool is configured to support the intraocular lens in a first position such that the first support part extends toward a tip of the tool body and the second support part extends toward a rear of the tool body, the intraocular lens insertion tool is configured to support the intraocular lens in a second position such that at least one of the first support part and the second support part is deformed by abutting against the abutting projection, the at least one of the first support part and the second support part is located closer to the optical part when the intraocular lens is in the second position than when the intraocular lens is in the first position, the placement part includes a placement surface with a first through-hole and a second through-hole, the placement surface being configured to receive the intraocular lens, a holding member, which includes the abutting projection and a holding projection is assembled to the placement part in a detachable manner so that the holding projection protrudes through the first through-hole of the placement surface to support the intraocular lens from below and the abutting projection protrudes from the placement surface through the second through-hole.

2. The intraocular lens insertion tool according to claim 1, wherein the first support part and the second support part are both located closer to the optical part when the intraocular lens is in the second position that when the intraocular lens is in the first position.

3. The intraocular lens insertion tool according to claim 1, wherein the intraocular lens is a one-piece type comprised of a soft synthetic resin material.

4. The intraocular lens insertion tool according to claim 1, wherein the placement surface is configured to receive the intraocular lens such that:

the abutting projection is disposed on the placement surface and closed to the optical part, the optical part is located at an end of the placement surface in a width direction on a front side of the tool body, and a tip portion of the first support part abuts against a surface of the abutting projection and faces the optical part when the intraocular lens is in the second position.

5. The intraocular lens insertion tool according to claim 1, wherein the placement surface is configured to receive the intraocular lens such that:

the abutting projection protrudes from the placement surface at a location close to the optical part, the optical part is located at an end of the placement surface in a width direction on a rear side of the tool body, and a tip portion of the second support part abuts against a surface of the abutting projection and faces the optical parts when the intraocular lens is in the second position.

6. The intraocular lens insertion tool according to claim 1, wherein:

the tool body further includes a lid member that is configured to cover the placement part, the abutting projection protrudes from a bottom surface of the placement part and toward the second support part, and a tip portion of the second support part abuts against the abutting projection such that the second support part deforms toward a rear surface side of the intraocular lens when the intraocular lens is in the second position.

7. The intraocular lens insertion tool according to claim 1, wherein the placement part includes a through-hole and the abutting projection is disposed through the through-hole.

8. The intraocular lens insertion tool according to claim 1, wherein:

the tool body includes a second abutting projection, the intraocular lens insertion tool is configured to support the intraocular lens in the second position such that the first support part is deformed by abutting against the abutting projection and the second support is deformed by abutting against the second abutting projection, and the first support and the second support part are both located closer to the optical part when the intraocular lens is in the second position than when the intraocular lens is in the first position.

* * * * *